(12) United States Patent
Fournier

(10) Patent No.: US 9,192,560 B2
(45) Date of Patent: Nov. 24, 2015

(54) STABLE COMPOSITION COMPRISING AN ANTI-AGEING COMPOUND AND A SOLVENT

(71) Applicant: Odile Fournier, Pantin Cedex (FR)

(72) Inventor: Odile Fournier, Pantin Cedex (FR)

(73) Assignee: CHANEL PARFUMS BEAUTE, Neuilly sur Seine (FR)

( * ) Notice: Subject to any disclaimer, the term of this patent is extended or adjusted under 35 U.S.C. 154(b) by 0 days.

(21) Appl. No.: 14/386,898

(22) PCT Filed: Apr. 10, 2013

(86) PCT No.: PCT/FR2013/050780
§ 371 (c)(1),
(2) Date: Sep. 22, 2014

(87) PCT Pub. No.: WO2013/153330
PCT Pub. Date: Oct. 17, 2013

(65) Prior Publication Data
US 2015/0038563 A1    Feb. 5, 2015

(30) Foreign Application Priority Data

Apr. 12, 2012   (FR) ...................................... 12 53356

(51) Int. Cl.
*A61K 8/49*   (2006.01)
*A61Q 19/08*  (2006.01)
*A61K 8/37*   (2006.01)
*A61K 8/40*   (2006.01)
*A61K 8/34*   (2006.01)

(52) U.S. Cl.
CPC ............... *A61K 8/4973* (2013.01); *A61K 8/342* (2013.01); *A61K 8/37* (2013.01); *A61K 8/40* (2013.01); *A61K 8/4986* (2013.01); *A61Q 19/08* (2013.01); *A61K 2800/10* (2013.01); *A61K 2800/52* (2013.01)

(58) Field of Classification Search
CPC ..................................................... A61K 8/4973
USPC ......................................................... 514/440
See application file for complete search history.

(56) References Cited

U.S. PATENT DOCUMENTS

| 2008/0139507 A1 | 6/2008 | Gupta |
| 2009/0215881 A1 | 8/2009 | Delaire et al. |
| 2011/0251242 A1 | 10/2011 | Bonda et al. |

FOREIGN PATENT DOCUMENTS

| WO | 2004103265 A2 | 12/2004 |
| WO | 2006134282 A1 | 12/2006 |
| WO | 2009010356 A1 | 1/2009 |
| WO | 2009129627 A1 | 10/2009 |

OTHER PUBLICATIONS

Hansen Solubility Parameters of Solvents, Industrial Solvents Handbook, 1996, pp. 35-56, XP000944977.
International Search Report, dated Feb. 17, 2014, from corresponding PCT application.

*Primary Examiner* — Taofiq A Solola
(74) *Attorney, Agent, or Firm* — Young & Thompson

(57) ABSTRACT

A cosmetic composition including diacetylresveratryl thioctate and a solvent. The solvent has a $_h$ value less than or equal to 8 and a $_d$ value greater than or equal to 16.9. Also, the use of the abovementioned composition to prevent and/or combat skin ageing.

9 Claims, No Drawings

STABLE COMPOSITION COMPRISING AN ANTI-AGEING COMPOUND AND A SOLVENT

The present invention relates to a stable cosmetic composition which preferably has no unpleasant odor, comprising diacetylresveratryl thioctate, a solvent and optionally an odor absorber. This composition is of use for preventing and/or combating skin aging.

The use of the diacetylresveratryl thioctate compound has been disclosed in patent application WO 2006/134282.

Nevertheless, the applicant has noted that this compound poses a problem of stability during its formulation, in particular if it is solubilized in a conventional lipophilic solvent of octyldodecanol type. As it happens, it would be desirable to be able to have stable cosmetic compositions comprising diacetylresveratryl thioctate.

The applicant has now discovered that this problem can be solved by using a specific solvent which has a $\delta_h$ value less than or equal to 8 and a $\delta_d$ value greater than or equal to 16.9 at ambient temperature.

The subject of the present invention is therefore a cosmetic care composition comprising:
diacetylresveratryl thioctate and
a solvent;
said solvent having a $\delta_h$ value less than or equal to 8 and a $\delta_d$ value greater than or equal to 16.9 at ambient temperature.

Such a solvent is preferably chosen from: trioctyl trimellitate, dimethyl isosorbide, ethylhexyl methoxycrylene, octocrylene, phenyl benzoate and mixtures thereof.

In one particular embodiment, the solvent is chosen from: polysorbate-20, trioctyl trimellitate, dimethyl isosorbide, ethylhexyl methoxycrylene, octocrylene, methyl trimellitate, phenyl benzoate and mixtures thereof.

The subject of the invention is also the use of a composition according to the invention for preventing and/or combating skin aging.

The diacetylresveratryl thioctate can be prepared as indicated in patent application WO 2006/134282.

The applicant has in fact discovered that diacetylresveratryl thioctate has a stability problem: when it is solubilized in a conventional solvent of octyldodecanol type, it recrystallizes.

However, it is essential to be able to have compositions in which diacetylresveratryl thioctate is stabilized.

The term "stabilization" is intended to mean an absence of crystallization of diacetylresveratryl thioctate after 10 days at 4° C. and six months at AT.

The term "AT", is intended to mean ambient temperature.

The term "ambient temperature" is intended to mean a temperature of approximately 25° C.

The characteristic of a solvent is described by five solution parameters: four Hansen solubility parameters ($\delta_d$, $\delta_p$, $\delta_h$ and $\delta_T$) and Log ($K_{ow}$).

The Hansen solubility parameters ($\delta_d$, $\delta_p$, $\delta_h$ and $\delta_T$) make it possible to predict whether one substance will be solubilized in another.

$\delta_d$ is a contribution due to the dispersion forces, $\delta_p$ is a contribution due to the polar forces, and $\delta_h$ is a hydrogen bond contribution. These parameters are defined as follows:

$$\delta_d = \left(\frac{\Delta E_d}{V}\right)^{1/2}$$

$$\delta_p = \left(\frac{\Delta E_p}{V}\right)^{1/2}$$

$$\delta_h = \left(\frac{\Delta E_h}{V}\right)^{1/2}$$

In this case, $\Delta E$ corresponds to the vaporization energy and V corresponds to the molar volume of the liquid.

$\delta_T$ is the solubility parameter due to the contribution of each of these parameters:

$$\delta_T = (\delta_d^2 + \delta_p^2 + \delta_h^2)^{1/2}$$

Log ($K_{ow}$) is a measure of the differential solubility of a chemical compound in two solvents (octanol and water) and corresponds to the octanol/water partition coefficient.

The applicant has now discovered that this problem can be solved by solubilizing the diacetylresveratryl thioctate in a particular solvent, which has a $\delta_h$ value less than or equal to 8 and a $\delta_d$ value greater than or equal to 16.9, at ambient temperature.

$\delta_h$ and $\delta_d$ in these ranges make it possible to ensure that said solvent facilitates the stable solubilization of diacetylresveratryl thioctate.

To the applicant's knowledge, it has never yet been suggested to use a solvent having a $\delta_h$ value less than or equal to 8 and a $\delta_d$ value greater than or equal to 16.9 at ambient temperature, for the purpose of stabilizing this active agent.

In one particular embodiment, the solvent of the cosmetic composition according to the present invention has a $\delta_p$ value between 4.7 and 7 at ambient temperature.

A $\delta_p$ value in this range makes it possible to ensure that said solvent facilitates the stable solubilization of the active agent.

In one particular embodiment, the solvent of the cosmetic composition according to the present invention has a $\delta_T$ value between 18 and 22 at ambient temperature.

A $\delta_T$ value in this range makes it possible to ensure that said solvent facilitates the stable solubilization of the active agent.

In one particular embodiment, the solvent of the cosmetic composition according to the present invention has a log ($K_{ow}$) value between 6 and 7.5 at ambient temperature.

A log($K_{ow}$) value in this range makes it possible to ensure that said solvent facilitates the stable solubilization of the active agent.

In one particular embodiment, the solvent of the cosmetic composition according to the present invention is chosen from: trioctyl trimellitate, dimethyl isosorbide, ethylhexyl methoxycrylene, octocrylene, phenyl benzoate and mixtures thereof.

In one particular embodiment, the solvent is chosen from: polysorbate-20, trioctyl trimellitate, dimethyl isosorbide, ethylhexyl methoxycrylene, octocrylene, methyl trimellitate, phenyl benzoate and mixtures thereof.

In one preferred embodiment, the solvent is octocrylene.

The diacetylresveratryl thioctate can be present, in the composition of the present invention, in a proportion ranging from 0.001% to 15% by weight, and preferably from 0.01% to 10% by weight, relative to the total weight of the composition.

The solvent can be present, in the composition of the present invention, in a proportion ranging from 0.1% to 50% by weight, and preferably from 1% to 25% by weight, relative to the total weight of the composition.

Although the diacetylresveratryl thioctate is physically stabilized by a solvent according to the invention, i.e. it is solubilized by said solvent without crystallization, the composition can pose an olfactory stability problem. Indeed, the development of an odor that is difficult to accept for a cosmetic product has been observed.

The applicant has now discovered that this problem can be solved by adding, to the composition described above, an odor scavenger chosen from: magnesium aluminum silicate hydrate, zinc oxide, kaolin, $Cu_2CO_3(OH)_2$ (or malachite), copper L-pyrrolidone carboxylate salt and mixtures thereof.

The term "odor scavenger" or "odor absorber" is intended to mean a molecule which has an affinity with sulfur and which makes it possible to neutralize the odor that is difficult to accept.

Thus, in one particular embodiment, the cosmetic composition of the present invention also comprises an odor absorber chosen from: magnesium aluminum silicate hydrate, zinc oxide, kaolin, $Cu_2CO_3(OH)_2$ (or malachite), copper L-pyrrolidone carboxylate salt, and mixtures thereof.

Preferably, an odor absorber is chosen from: kaolin, copper L-pyrrolidone carboxylate salt and mixtures thereof.

The odor absorber may be present, in the composition of the present invention, in a proportion ranging from 0.0006% to 6% by weight, and preferably from 0.006% to 0.6% by weight, relative to the total weight of the composition.

In addition to the diacetylresveratryl thioctate, the specific solvent and preferably an odor absorber previously described, the cosmetic composition according to the invention may also comprise at least one additive which is customary in the cosmetics or pharmacy field, for instance a compound chosen from a gelling and/or thickening agent, a surfactant or co-surfactant, a liquid fatty substance or an oil, a wax, a silicone elastomer, a sunscreen, a dye, a matting agent or a filler, a pigment, a tensioning agent, a preservative, a sequestering agent, a fragrance, and mixtures thereof.

In particular, according to one preferred embodiment, the cosmetic composition according to the invention may comprise, in a nonlimiting manner, one or more of the following additives:

one or more aqueous-phase gelling and/or thickening agent(s), chosen, for example, from hydrophilic or amphiphilic, crosslinked or noncrosslinked homopolymers and copolymers of acryloylmethylpropanesulfonic acid (AMPS) and/or of acrylamide and/or of acrylic acid and/or of acrylic acid salts or esters, such as ammonium acryloyldimethyltaurate/VP copolymer and ammonium acryloyldimethyltaurate/beheneth-25 methacrylate copolymer, in particular those sold under the names Aristoflex® AVC and HMB from Clariant, or else the acrylates/C10-30 alkyl acrylate crosspolymer sold under the tradename PEMULEN® TR-1 or TR-2, Carbopol® 1382, or Carbopol® Ultrez 20 by the company Novéon, cellulose-based derivatives, gums of vegetable origin (acacia or arabic, agar, guar, locust bean, alginates, carrageenans, pectin) or of microbial origin (xanthan, pullulan), clays (laponite). Said gelling and/or thickening agent may be present in the composition in a content of about from 0.01% to 5% by weight, relative to the total weight of the composition;

one or more surfactant(s), preferably emulsifying surfactant(s), whether they are nonionic, anionic, cationic or amphoteric, and in particular fatty acid esters of polyols, such as oxyalkylenated (more particularly polyoxyethylenated) fatty acid esters of glycerol, oxyalkylenated fatty acid esters of sorbitan, oxyalkylenated (oxyethylenated and/or oxypropylenated) fatty acid esters, for instance the PEG-100 stearate/glyceryl stearate mixture sold, for example, by the company Croda under the name Arlacel® 165 and fatty acid esters of sucrose, for instance sucrose stearate; fatty alcohol ethers of a sugar, in particular alkylpolyglucosides (APGs), such as decyl glucoside and lauryl glucoside, cetostearyl glucoside optionally as a mixture with cetostearyl alcohol, sold for example under the name Montanov® 68 by the company SEPPIC, and also arachidyl glucoside, for example in the form of the mixture of arachidyl and behenyl alcohols and of arachidyl glucoside, sold under the name Montanov® 202 by the company SEPPIC; fatty alcohol ethers of polyethylene glycol; polyether-modified polysiloxanes; betain and derivatives thereof; polyquaterniums; ethoxylated fatty alcohol sulfate salts; sulfosuccinates; sarcosinates; alkyl phosphates and dialkyl phosphates, and salts thereof; and fatty acid soaps. Said surfactant may be present in the composition in a content of about from 0.1% to 8%, preferably 0.5% to 3% by weight, relative to the total weight of the composition;

one or more cosurfactant(s), such as linear fatty alcohols comprising a long carbon chain ($C_{14}$-$C_{20}$) and in particular cetyl and stearyl alcohols, said surfactant being present in the composition in a proportion of from 0.1% to 5%, preferably 0.5% to 2% by weight, relative to the total weight of the composition;

one or more fatty substance(s) that is(are) liquid at ambient temperature, commonly called oil(s), which are volatile or nonvolatile, hydrocarbon-based or silicone-based, and linear, cyclic or branched, for example silicone oils such as polydimethylsiloxanes (dimethicones), polyalkylcyclosiloxanes (cyclomethicones) and polyalkylphenylsiloxanes (phenyl dimethicones); synthetic oils such as fluoro oils, alkyl benzoates and branched hydrocarbons such as polyisobutylene or isododecane; mineral oils (paraffin); vegetable oils (sweet almond oil, macadamia oil, blackcurrant seed oil, jojoba oil or else Camelina sativa oil, such as the oil sold under the tradename Lipex® Omega 3/6 by the company Unipex); fatty alcohols; fatty amides; fatty acids or esters, for instance the $C_{12}$-$C_{15}$ alkyl benzoate sold under the tradename Finsolv® TN by the company Innospec, triglycerides, including those of capric/caprylic acids, the dicaprylyl carbonate sold under the name Cetiol® CC by the company Cognis; preferably in a proportion of from 0.1% to approximately 10%, preferably from 0.5% to 5% by weight, relative to the total weight of the composition;

one or more waxes (compound which is solid or substantially solid at ambient temperature), the melting point of which is generally above 35° C., such as ozokerite, polyethylene wax, beeswax or carnauba wax, preferably in a proportion of from 0.01% to approximately 5%, preferably 0.5% to 5% by weight, relative to the total weight of the composition;

one or more silicone elastomer(s) obtained in particular by reacting, in the presence of a catalyst, a polysiloxane having at least one reactive group (hydrogen or vinyl, in particular) and bearing at least one alkyl (in particular methyl) or phenyl group, which is on the end and/or on the side, with an organosilicone such as an organohydrogenopolysiloxane, preferably in a proportion of from 0.1% to approximately 20%, preferably 0.25% to 15% by weight, relative to the total weight of the composition;

one or more sunscreen(s), in particular organic screens, such as dibenzoylmethane derivatives (including the butyl methoxydibenzoylmethane sold in particular by DSM under the tradename Parsol® 1789), cinnamic acid derivatives (including the ethylhexyl methoxycinnamate sold in particular by DSM under the tradename Parsol® MCX), salicylates, para-aminobenzoic acids, β,β'-diphenyl acrylates, benzophenones, benzylidenecamphor derivatives, phenylbenzimidazols, triazines, phenylbenzotriazols and anthranilic derivatives; or inorganic screens, based on inorganic oxides in the form of pigments or of nanopigments, which are coated or uncoated, and in particular based on titanium dioxide or on zinc oxide; preferably in a proportion of from 0.1% to approximately 30%, better still from 0.5% to 20% by weight, relative to the total weight of the composition;

one or more water-soluble dye(s), such as, for example, ponceau disodium salt, alizarin green disodium salt, quinoline yellow, amaranth trisodium salt, tartrazine disodium salt, rhodamine monosodium salt, fuchsin disodium salt or xanthophyll, preferably in a proportion of from 0.1% to approximately 2% by weight, relative to the total weight of the composition;

one or more fillers, in particular matting agents or soft-focus-effect fillers, and in particular soft-focus-effect powders.

The term "filler" should be understood to mean lamellar or nonlamellar, inorganic or synthetic, colorless or white particles suitable for giving the composition body or stiffness and/or softness, mattness and uniformity immediately on application. These fillers can in particular modify or even mask wrinkles through a camouflage effect, or a soft-focus effect.

The matting agents may be chosen from matting polymers, (in solution, in dispersion or in particle form) and inorganic particles which reduce the shininess of the skin and unify the complexion. The matting agent may in particular be chosen from a starch, talc, cellulose microbeads, vegetable fibers, synthetic fibers, in particular polyamide fibers (Nylon® powders such as Nylon-12 (Orgasol® sold by the company Atochem), microspheres of acrylic copolymers, in particular of poly(methyl (meth)acrylate) (PMMA particles or Micropearl® M310 particles sold by the company SEPPIC), silica powders, silicone resin powders, acrylic polymer powders, polyethylene powders, elastomeric crosslinked organopolysiloxanes (sold in particular under the name KSG® by the company Shin-Etsu, under the names Trefil®, BY29® or EPSX® by the company Dow Corning or under the name Gransil® by the company Grant Industries), talc/titanium dioxide/alumina/silica composite powders, silicate powders, and mixtures thereof.

The soft-focus-effect filler may give transparency to the complexion and a hazy effect. Preferably, the soft-focus fillers have an average particle size less than or equal to 30 microns, more preferentially less than or equal to 15 microns. These soft-focus fillers may be of any shape and in particular may be spherical or nonspherical. They may be chosen from powders of silica and silicates, in particular of alumina, powders of poly(methyl methacrylate) type (PMMA or Micropearl® M310), talc, silica/$TiO_2$ or silica/zinc oxide composites, polyethylene powders, starch powders, polyamide powders, styrene/acrylic copolymer powders, silicone elastomers, and mixtures thereof.

Preferably, these matting agents or soft-focus-effect fillers are used in a proportion of from 0.1% to approximately 10% by weight, relative to the total weight of the composition, preferably in a proportion of from 0.1% to approximately 7% by weight;

one or more white or colored, nacreous or non nacreous, inorganic and/or organic, coated or uncoated pigments which are insoluble in the medium, and which are intended to color and/or opacify the composition. They may be of usual or nonometric size. Among the inorganic pigments, mention may be made of titanium dioxide, which has optionally been surface-treated, iron or chromium oxides, manganese violet, ultramarine blue, chromium hydrate and ferric blue. Among the organic pigments, mention may be made of carbon black, pigments of D&C type, and lakes based on cochineal carmine, barium, strontium, calcium or aluminum. Nacreous pigments or nacres are iridescent particles which reflect light. These nacreous pigments may be chosen from white nacreous pigments such as mica coated with titanium or with bismuth oxichloride, and colored nacreous pigments such as titanium mica with iron oxides. The pigments may have undergone a surface treatment. Preferably, these pigments are used in a proportion of from 0.1% to approximately 10% by weight, relative to the total weight of the composition, preferably in a proportion of from 0.1% to approximately 5% by weight;

one or more tensioning agents. The term "tensioning agent" should be understood to mean a compound suitable for tightening the skin and, via this tensioning effect, smoothing the skin and immediately causing the wrinkles and fine lines therein to be reduced or even to disappear. As tensioning agents, mention may be made of polymers of natural origin; mixed silicates; colloidal particles of inorganic fillers; synthetic polymers; and mixtures thereof. Mention may in particular be made of: polymers of vegetable or microbial origin, polymers derived from skin appendages, egg proteins, and latexes of natural origin. These polymers are preferably hydrophilic. As polymers of vegetable origin, mention may in particular be made of proteins and protein hydrolysates, and more particularly extracts of cereals, of leguminous plants and of oil-producing plants, such as extracts of corn, of rye, of soft wheat, of buckwheat, of sesame, of spelt, of pea, of tapioca, of broad bean, of lentil, of soya and of lupin. Other tensioning agents which can be used according to the invention are polysaccharides of natural origin, in particular starch derived in particular from rice, from corn, from tapioca, from potato, from cassava, from pea; carrageenans, acacia gums (gum arabic), alginates, agars, gellans, xanthan gums, cellulose-based polymers and pectins, advantageously as an aqueous dispersion of gel microparticles, cellulose-based derivatives, and mixtures thereof. The synthetic polymers are generally in the form of a latex or of a pseudo latex and can be of polycondensate type or obtained by a free-radical polymerization. Mention may in particular be made of polyester/polyurethane and polyether/polyurethane dispersions. Preferably, the tensioning agent is a copolymer of PVP/dimethiconyl acrylate and of hydrophilic polyurethane (Aquamere® S-2011® from the company Hydromer). More preferentially, the tensioning agent is a *Manihot esculenta* tuber extract (sold under the name Instensyl by Silab);

one or more preservative(s);
sequestering agents such as EDTA salts;
fragrances;
and mixtures thereof.

Examples of such additives are mentioned in particular in the CTFA dictionary (International Cosmetic Ingredient Dictionary and Handbook published by The Cosmetic, Toiletry and Fragrance Association, $11^{th}$ Edition, 2006) which describes a great variety, without limitation, of cosmetic and pharmaceutical ingredients normally used in the skincare industry, which are suitable for use as additional ingredients in the compositions according to the present invention.

Those skilled in the art are able to choose, from all of these optional additives, both the composition and the amount of those that will be added to the composition, such that the latter retains all of its properties.

In addition, the composition according to the present invention may optionally contain various active agents which can be chosen from the group consisting of vitamins, antioxidants, moisturizing agents, antipollution agents, keratolytic agents, astringents, anti-inflammatories, bleaching agents and microcirculation-promoting agents.

Examples of vitamins include vitamins A, B1, B2, B6, C and E and derivatives thereof, pantothenic acid and its derivatives and biotin.

Examples of antioxidants include ascorbic acid and its derivatives, such as ascorbyl palmitate, ascorbyl tetraisopalmitate, ascorbyl glucoside, magnesium ascorbyl phosphate, sodium ascorbyl phosphate and ascorbyl sorbate; tocopherol and its derivatives, such as tocopheryl acetate, tocopheryl sorbate and other tocopherol esters; BHT and BHA; esters of gallic acid, phosphoric acid, citric acid, maleic acid, malonic acid, succinic acid, fumaric acid, cephalin, hexametaphosphate, phytic acid, and extracts of plants, for example of roots of *Zingiber officinale* (ginger), such as the Blue Malagasy Ginger sold by the company Biolandes, of *Chondrus crispus, Rhodiola, Thermus thermophilus*, maté leaf, oak wood, kayu rapet bark, sakura leaves and ylang ylang leaves.

Examples of moisturizing agents include polyethylene glycol, propylene glycol, dipropylene glycol, glycerol, butylene glycol, xylitol, sorbitol, maltitol, mucopolysaccharides, such as chondroitin sulfuric acid, hyaluronic acid of high or low molecular weight or else hyaluronic acid potentiated with a silanol derivative, such as the active agent Epidermosil® sold by the company Exymol, and mucoitin sulfuric acid; caronic acid; bile salts, a principal component of NMF (natural moisturizing factor) such as a salt of pyrrolidonecarboxylic acid and a salt of lactic acid, an amino acid analog such as urea, cysteine and serine; a short-chain soluble collagen, diglycerol PPGs, homo and copolymers of 2-methacryloyloxyethylphosphorylcholine such as Lipidure HM and Lipidure PBM from NOF; allantoin; glycerol derivatives such as PEG/PPG/polybutylene glycol-8/5/3 glycerol from NOF, sold under the tradename Wilbride®S753 or else the glyceryl polymethacrylate from Sederma sold under the tradename Lubrajel® MS; the trimethylglycine sold under the tradename Aminocoat® by the company Asahi Kasei Chemicals and various plant extracts, such as extracts of *Castanea sativa*, hydrolyzed hazelnut proteins, *Tuberosa polyanthus* polysaccharides, *Argania spinosa* kernel oil and extracts of nacre containing a conchiolin; which are sold in particular by the company Maruzen (Japan) under the tradename Pearl Extract®.

Other examples of moisturizing agents include compounds which stimulate the expression of matriptase MT/SP1, such as an extract of locust bean pulp, and also agents which stimulate the expression of FN3K; agents which increase keratinocyte proliferation or differentiation, such as extracts of *Thermus thermophiles* or of *Camellia japonica* Alba Plena flower or of *Theobroma cacao* bean shells, water-soluble corn extracts, peptide extracts of *Voandzeia subterranea* and niacinamide; epidermal lipids and agents which increase epidermal lipid synthesis, either directly, or by stimulating certain β-glucosidases which modulate the deglycosylation of lipid precursors, for instance glucosylceramide to ceramides, such as phospholipids, ceramides, or lupin protein hydrolysates.

Examples of antipollution agents include Moringa pterygosperma seed extract (for example Purisoft® from LSN); Shea butter extract (for example Detoxyl® from Silab), and a mixture of ivy extract, phytic acid and sunflower seed extract (for example Osmopur® from Sederma).

Examples of keratolytic agents include α-hydroxy acids (for example glycolic, lactic, citric, malic, mandelic, or tartaric acids) and β-hydroxy acids (for example salicylic acid), and esters thereof, such as $C_{12}$-$C_{13}$ alkyl lactates, and plant extracts containing these hydroxy acids, such as Hibiscus sabdriffa extracts.

Examples of anti-inflammatory agents include bisabolol, allantoin, tranexamic acid, zinc oxide, sulfur oxide and its derivatives, chondroitin sulfate, glycyrrhizinic acid and its derivatives such as glycyrrhizinates.

Examples of astringents include hamamelis extracts.

Examples of bleaching agents include arbutin and its derivatives, ferulic acid (such as Cytovector®: water, glycol, lecithin, ferulic acid, hydroxyethylcellulose, sold by BASF) and its derivatives, kojic acid, resorcinol, ellagic acid, leucodopachrome and its derivatives, vitamin B3, linoleic acid and its derivatives, ceramides and homologs thereof, a peptide as described in patent application WO 2009/010356, a bioprecursor as described in patent application WO 2006/134282 or a tranexamate salt such as the hydrochloride salt of cetyl tranexamate, a licorice extract (*Glycyrrhiza glabra* extract), which is sold in particular by the company Maruzen under the tradename Licorice Extract®, a bleaching agent that also has an antioxidant effect, for instance vitamin C compounds, including ascorbate salts, ascorbyl esters of fatty acids or of ascorbic acid, and other derivatives of ascorbic acid, for example ascorbyl phosphates, such as magnesium ascorbyl phosphate and sodium ascorbyl phosphate, or sorbic acid saccharide esters, which include, for example, ascorbyl-2-glucoside, 2-O-alpha-D-glucopyranosyl-ascorbate or 6-O-beta-D-galactopyranosyl-ascorbate. An active agent of this type is sold in particular by the company DKSH under the tradename Ascorbyl Glucoside®.

Examples of microcirculation-promoting agents include an extract of lupin (such as Eclaline® from Silab), of ruscus, of horse chestnut, of ivy, of ginseng or of sweet clover, caffeine, nicotinate and its derivatives, a *Corallina officinalis* algal extract such as the one sold by CODIF; and mixtures thereof. These agents which are active on skin microcirculation can be used to prevent dulling of the complexion and/or to improve the uniformity and the radiance of the complexion.

The composition used according to the invention may also comprise, in addition to the polypeptide according to the invention, at least one active agent chosen from: agents which stimulate tensin 1 expression, such as an elemi extract; agents which stimulate FN3K expression and/or FN3K RP expression, such as a *Butea frondosa* extract; agents which stimulate CERT or ARNT2 expression; agents which stimulate growth factor production; anti-glycation or deglycating agents; agents which increase collagen synthesis or which prevent collagen degradation (anti-collagenase agents, especially matrix metalloproteinase inhibitors); in particular agents which increase collagen IV and/or hyaluronan and/or fibronectin synthesis, such as at least one acylated oligopeptide, in particular the one sold by the company Sederma under the tradename Matrixyl® 3000; agents which increase elastin synthesis or which prevent elastin degradation (anti-elastase agents); agents which increase glycosaminoglycan or proteoglycan synthesis or which prevent the degradation thereof (anti-proteoglycanase agent) such as the active agent Epidermosil® (hyaluronic acid combined with methylsilanetriol) sold by the company Exsymol; agents which stimulate integrin synthesis by fibroblasts; agents which increase fibroblast proliferation; agents which facilitate percutaneous absorption, such as alcohols, fatty alcohols and fatty acids, and ester or ether derivatives thereof, pyrrolidones, 4-alkyl-oxazolidin-2-ones, such as 4-decyloxazolidin-2-one; terpenes, essential oils and α-hydroxy acids; and mixtures thereof, without this list being limiting.

The invention will now be illustrated by means of the following nonlimiting examples.

EXAMPLES

Example 1-a

Choice of Solvent

Candidate solvents were chosen using the HSPiP software (Version: 3.1.14).

The candidate solvents thus chosen are then subjected to the stabilization test. This test consists in comparing the initial solubility ($t_0$) and the solubility a day later (1D) at ambient temperature (AT).

Results

The following table gives the values of the solubilization parameters of each candidate solvent ($\delta_h$, $\delta_d$, $\delta_p$, $\delta_T$ and log ($K_{ow}$) at ambient temperature) and the results of the diacetylresveratryl thioctate stabilization tests.

|  | Solubilization parameters | | | | Log | Solubility | | |
|---|---|---|---|---|---|---|---|---|
|  | $\delta_h$ | $\delta_d$ | $\delta_p$ | $\delta_T$ | ($K_{ow}$) | $t_0$/AT | 1 D/AT | Stability |
| Trioctyl trimellitate | 2.1 | 16.9 | 4.7 | 18 | 9.71 | Partially soluble | Clear | Yes |
| Dimethyl isosorbide | 7.6 | 17.5 | 7.4 | 20 | −0.43 | Partially soluble | Clear | Yes |
| Ethylhexyl methoxycrylene | 6.4 | 18.1 | 6.8 | 20.2 | 6.99 | Partially soluble | Clear | Yes |
| Octocrylene | 5.6 | 18.2 | 6.6 | 19.5 | 6.96 | Partially soluble | Clear | Yes |
| Phenyl benzoate | 4.5 | 19.5 | 5.8 | 21 | 4.22 | Partially soluble | Clear | Yes |
| Octyldodecanol | 9 | 16.1 | 3.8 | 19.1 | 8.84 | Insoluble | Precipitate | No |
| PPG-15 stearyl ether | 8.2 | 16.4 | 5.8 | 19.5 | 8.35 | Insoluble | Precipitate | No |

Among the solvents tested, diacetylresveratryl thioctate is partially soluble at $t_0$ and at AT in trioctyl trimellitate, dimethyl isosorbide, ethylhexyl methoxycrylene, octocrylene and phenyl benzoate. The diacetylresveratryl thioctate is stably solubilized one day after (1D) the dissolution.

It should be noted that all these solvents meet the conditions $\delta_h \leq 8$ and $\delta_d \geq 6.9$ at ambient temperature, whereas octyldodecanol and PPG-15 stearyl ether have $\delta_h$ and $\delta_d$ values outside these ranges.

Among the five solvents having demonstrated positive results, ethylhexyl methoxycrylene and octocrylene are particularly satisfactory.

It should be noted that these two solvents meet, in addition to the two conditions $\delta_h \leq 8$ and $\delta_d \geq 6.9$ at ambient temperature, the following additional conditions: $4.7 \leq \delta_p \leq 7.5$, $18 \leq \delta_T \leq 22$ and $6 \leq \log(K_{ow}) \leq 7.5$ at ambient temperature.

Octocrylene was chosen for the following examples.

Example 1-b

Comparative Example

The stabilization of resveratrol by dimethyl isosorbide, ethylhexyl methoxycrylene and octocrylene was evaluated according to the same protocol as Example 1-a, except that the solubility was evaluated on the same day as $t_o$ (0D).

Results

The table on the following page gives the values of the solubilization parameters of each solvent tested ($\delta_h$, $\delta_d$, $\delta_p$, $\delta_T$ and log ($K_{ow}$) at ambient temperature) and the results of the resveratrol stabilization tests.

In conclusion, the resveratrol active agent precipitates for the three solvents tested.

|  | Solubilization parameters | | | | Log | Solubility | | |
|---|---|---|---|---|---|---|---|---|
|  | $\delta_h$ | $\delta_d$ | $\delta_p$ | $\delta_T$ | ($K_{ow}$) | $t_0$/AT | 0 D/AT | Stability |
| Dimethyl isosorbide | 7.6 | 17.5 | 7.4 | 20 | −0.43 | Partially soluble | Precipitate | No |
| Ethylhexyl methoxycrylene | 6.4 | 18.1 | 6.8 | 20.2 | 6.99 | Soluble fraction | Precipitate | No |
| Octocrylene | 5.6 | 18.2 | 6.6 | 19.5 | 6.96 | Soluble fraction | Precipitate | No |

Example 2

Choice of Odor Absorber

Odor absorbers were selected according to the following protocol.

Protocol

The composition of the following base was prepared. In this composition, octocrylene is used as diacetylresveratryl thioctate-stabilizing solvent.

| | |
|---|---|
| Demineralized water | 85.75% |
| Guar gum | 0.30% |
| Sodium acrylate/acryloyldimethyl taurate/ dimethylacrylamide crosspolymer & isohexadecane & Polysorbate 60 (Simulgel SMS 88) | 1.50% |
| Glycerol | 2.00% |
| Disodium EDTA (Dissolvine NA-2) | 0.05% |
| Phenoxyethanol | 0.70% |

-continued

| | |
|---|---|
| Diacetylresveratryl thioctate | 0.10% |
| Trioctyl Trimellitate (Biosynth Totm) | 3.00% |
| Dimyristyl tartrate/Cetearyl alcohol - C12-15 Pareth 7 - PPG 25 Laureth 25 (Cosmacol PSE) | 2.00% |
| Octocrylene | 4.00% |

0.60% of each candidate odor absorber was added to the above base.

Firstly, the initial odor ($t_o$) was evaluated at ambient temperature (AT).

For the solvents of which the results of this first evaluation were positive, a second olfactory evaluation was carried out 15 days later at 45° C. (15D/45° C.)

Results

The results are summarized in the table below.

| Odor absorber | $t_0$/AT | 15 D/45° C. |
|---|---|---|
| Magnesium aluminum silicate hydrate | Yes | Yes |
| Zinc oxide | Yes | Yes |
| Kaolin | Yes | Yes |
| Copper and silica powder | Yes | Yes |
| $Cu_2CO_3(OH)_2$ (or malachite) | Yes | Yes |
| Silica | No | — |
| Aluminum hydrate | No | — |
| Zinc gluconate | No | — |
| $Cu_2CO_3(OH)_2$ (or malachite) + EDTA | No | — |
| Poly(methyl methacrylate) | No | — |
| Bis-ethylhexyl hydroxydimethoxy benzylmalonate | No | — |
| Zinc L-pyrrolidone carboxylate salt | No | — |

After the first olfactory evaluation at ambient temperature at $t_0$ ($t_0$/AT), the magnesium aluminum silicate hydrate, the zinc oxide, the kaolin, the copper and silica powder, and the $Cu_2CO_3(OH)_2$ (or malachite) were retained.

After the second evaluation 15 days later at 45° C. (15D/45° C.), satisfactory results were obtained for these compounds.

Example 3

Study of Olfactory Stability

For the odor absorbers retained in example 2 (magnesium aluminum silicate hydrate, zinc oxide, kaolin, copper and silica powder, copper L-pyrrolidone carboxylate salt and $Cu_2CO_3(OH)_2$ (or malachite)) and also for the copper L-pyrrolidone carboxylate salt, a more detailed olfactory stability study was carried out according to the following protocol.

Protocol

A Base composition as follows was prepared. In this composition, octocrylene is used as diacetylresveratryl thioctate-stabilizing solvent.

Base

| | |
|---|---|
| Demineralized water (90.34% for the copper L-pyrrolidone carboxylate salt) | 89.80% |
| Guar gum | 0.30% |
| Sodium acrylate/acryloyldimethyl taurate/ dimethylacrylamide crosspolymer & isohexadecane & Polysorbate 60 (Simulgel SMS 88) | 1.50% |
| Glycerol | 2.00% |
| Phenoxyethanol | 0.70% |
| Dimyristyl tartrate/Cetearyl alcohol - C12-15 Pareth 7 - PPG 25 Laureth 25 (Cosmacol PSE) | 1.00% |
| Diacetylresveratryl thioctate | 0.10% |
| Octocrylene | 4.00% |

0.6% of each candidate odor absorber was added to one of the base compositions above and the olfactory stability was tested at three temperatures (ambient temperature, 5° C. and 45° C.) and at the following times:

at the beginning ($t_o$),
1 month (1M),
2 months (2M) and
3 months (3M).

The table below gives the results. The results at $t_0$, 1 month (1M) and 3 months (3M) are given in a single column for the three temperatures tested, since the results are identical.

Results

The results are summarized in the table below.

| Base | $t_0$ | 1 M | 2 M AT | 2 M 5° C. | 2 M 45° C. | 3 M |
|---|---|---|---|---|---|---|
| Reference (Base) | Yes | Yes | No | No | No | No |
| Magnesium aluminum silicate hydrate | Yes | No | No | No | No | No |
| Zinc oxide | Yes | Yes | Yes | Yes | No | No |
| Kaolin | Yes | Yes | Yes | Yes | Yes | Yes |
| $Cu_2CO_3(OH)_2$ (or malachite) | Yes | Yes | Yes | Yes | Yes | Yes |
| Copper L-pyrrolidone carboxylate salt | Yes | Yes | Yes | Yes | Yes | Yes |

The results show that the mixture of Base with magnesium aluminum silicate hydrate loses its effectiveness at one month (1M). Likewise, beyond two months (2M and 3M), the mixtures of Base with zinc oxide are no longer effective.

In the end, kaolin and $Cu_2CO_3(OH)_2$ (or malachite) give satisfactory results. The copper L-pyrrolidone carboxylate salt is the most appropriate in combination with the Base.

Example 4

Stability of Diacetylresveratryl Thioctate in the Formulation

A diacetylresveratryl thioctate stability test was carried out for the odor absorbers retained in Example 3, according to the following protocol, for the purpose of confirming the compatibility between the solvent and the odor absorber.

Protocol 0.6% of each candidate odor absorber was added to the Base and the olfactory stability was tested at two temperatures (5° C. and 45° C.) at two months.

Results

The results are given in the table below.

| Base | 5° C. | 45° C. |
|---|---|---|
| Control without odor absorber (Base) | 0.098 | 0.095 |
| Magnesium aluminum silicate hydrate | 0.096 | 0.094 |
| Zinc oxide | 0.094 | 0.064 |
| Kaolin | 0.095 | 0.09 |
| $Cu_2CO_3(OH)_2$ (or malachite) | 0.097 | 0.085 |
| Copper L-pyrrolidone carboxylate salt | 0.1 | 0.094 |

At 5° C., satisfactory results were obtained for all the absorbers tested, whereas, at 45° C., zinc oxide disrupts the stabilization of the diacetylresveratryl thioctate. A degree of diacetylresveratryl thioctate stabilization greater than or equal to 0.085 was obtained for the magnesium aluminum silicate hydrate, the kaolin, the $Cu_2CO_3(OH)_2$ (or malachite) and the copper L-pyrrolidone carboxylate salt.

Example 5

Formula According to the Invention

The following composition is a water-in-oil emulsion and was prepared for preventing and/or combating skin aging.

| | |
|---|---|
| Water | qs 100 |
| Alcohol | 10% |
| Glycerol | 2% |
| Phenoxyethanol | qs |
| Octyldodecanol | 4% |
| Ammonium acryloyldimethyltaurate/VP copolymer (Aristoflex AVC) | 1% |
| Kaolin (Whitetex) | 0.6% |
| Copper L-pyrrolidone carboxylate salt) (Cuivridone) | 0.06% |
| Octocrylene | 3% |
| Diacetylresveratryl thioctate (reversage) | 0.1% |
| *Centella* heterosides | 3% |

The invention claimed is:

1. A cosmetic composition comprising:
   diacetylresveratryl thioctate; and
   a solvent selected from the group consisting of trioctyl trimellitate, dimethyl isosorbide, ethylhexyl methoxycrylene, octocrylene, phenyl benzoate and mixtures thereof, wherein said solvent has a $\delta_h$ value less than or equal to 8 and a $\delta_d$ value greater than or equal to 16.9 at ambient temperature.

2. The cosmetic composition as claimed in claim 1, further comprising an odor absorber selected from the group consisting of: magnesium aluminum silicate hydrate, zinc oxide, kaolin, $Cu_2CO_3(OH)_2$ (or malachite), copper L-pyrrolidone carboxylate salt, and mixtures thereof.

3. The cosmetic composition as claimed in claim 1, wherein the diacetylresveratryl thioctate is in a proportion ranging from 0.001% to 15% by weight, relative to the total weight of the composition.

4. The cosmetic composition as claimed in claim 1, wherein the solvent is in a proportion ranging from 0.1% to 50% by weight, relative to the total weight of the composition.

5. The cosmetic composition as claimed in claim 1, wherein the odor absorber is in a proportion ranging from 0.0006% to 6% by weight, relative to the total weight of the composition.

6. A method for combating skin aging, comprising applying to the skin of a subject in need thereof the cosmetic composition as claimed in claim 1.

7. The cosmetic composition as claimed in claim 1, wherein the diacetylresveratryl thioctate is in a proportion ranging from 0.01% to 10% by weight, relative to the total weight of the composition.

8. The cosmetic composition as claimed in claim 1, wherein the solvent is in a proportion ranging from 1% to 25% by weight, relative to the total weight of the composition.

9. The cosmetic composition as claimed in claim 1, wherein the odor absorber is in a proportion ranging from 0.006% to 0.6% by weight, relative to the total weight of the composition.

* * * * *